US012680130B2

(12) United States Patent
Blomquist et al.

(10) Patent No.: US 12,680,130 B2
(45) Date of Patent: Jul. 14, 2026

(54) DEVICES AND METHODS FOR EXTRACTION-FREE PATHOGEN TESTING

(71) Applicants: Transformative Biotech, LLC, Boulder, CO (US); THE REGENTS OF THE UNIVERSITY OF COLORADO, Aurora, CO (US)

(72) Inventors: Robert E. Blomquist, Boulder, CO (US); Shi-Long Lu, Englewood, CO (US); Brian L. Harry, Denver, CO (US); Xin Yao, Boulder, CO (US)

(73) Assignees: Transformative Biotech, LLC, Boulder, CO (US); The Regents of the University of Colorado, Aurora, CO (US)

( * ) Notice: Subject to any disclaimer, the term of this patent is extended or adjusted under 35 U.S.C. 154(b) by 944 days.

(21) Appl. No.: 17/864,160

(22) Filed: Jul. 13, 2022

(65) Prior Publication Data

US 2023/0026556 A1     Jan. 26, 2023

Related U.S. Application Data

(60) Provisional application No. 63/226,531, filed on Jul. 28, 2021, provisional application No. 63/221,448, filed on Jul. 13, 2021.

(51) Int. Cl.
| | |
|---|---|
| *C12Q 1/686* | (2018.01) |
| *C12Q 1/6853* | (2018.01) |
| *C12Q 1/6888* | (2018.01) |
| *C12Q 1/70* | (2006.01) |

(52) U.S. Cl.
CPC ........... *C12Q 1/686* (2013.01); *C12Q 1/6853* (2013.01); *C12Q 1/6888* (2013.01); *C12Q 1/70* (2013.01); *C12Q 2600/112* (2013.01)

(58) Field of Classification Search
None
See application file for complete search history.

(56) References Cited

U.S. PATENT DOCUMENTS

| | | | |
|---|---|---|---|
| 4,353,868 | A | 10/1982 | Joslin et al. |
| 4,683,195 | A | 7/1987 | Mullis et al. |
| 4,683,202 | A | 7/1987 | Mullis |
| 11,040,340 | B1 | 6/2021 | Moore |
| 11,965,218 | B2 * | 4/2024 | Foxman .................... C12Q 1/70 |
| 2019/0144516 | A1 * | 5/2019 | Lengyel ................. A61K 45/06 |
| | | | 424/85.2 |
| 2022/0290210 | A1 | 9/2022 | Blomquist et al. |

FOREIGN PATENT DOCUMENTS

| | | |
|---|---|---|
| WO | 2020/160317 A1 | 8/2020 |
| WO | 2021/133943 A1 | 7/2021 |
| WO | 2021/246820 A1 | 12/2021 |
| WO | 2022/192440 A1 | 9/2022 |
| WO | 2023/081029 A9 | 10/2024 |

OTHER PUBLICATIONS

Wei et al. (Jan. 28, 2021, Scientific reports, 11(1), 2402, pp. 1-6).*
Lalli et al. (Epub Aug. 6, 2020, MedRxiv, pp. 1-34).*
To et al. (2020, The Lancet infectious diseases, 20(5), pp. 565-574).*
European Centre for Disease Prevention and Control, 2021, Methods for the detection and identification of SARS-CoV-2 variants, [online], Retrieved [Sep. 26, 2022] Retrieved from the Internet: [https://www.ecdc.europa.eu/sites/default/files/documents/Methods-for-the-detection-and-identification-of-SARS-CoV-2-variants.pdf], 7 pages.
FDA, Emergency use Authorization (EUA) Summary Omnigene-Oral OM-505 and OME-505 Saliva Collection Devices, Publication [online] Oct. 28, 2020, Retrieved [Sep. 26, 2022] Retrieved from the Internet: [https://www.fda.gov/media/143419/download#:':text= This%20sample%20collection%20device%20has%20been% 20authorized%20by%20FDA%20under%20an%20EUA.&text= This%20sample%20collection%20device%20has,any%20other% 20viruses%20or%20pathogens.], 10 pages.
Griesemer, 2021, Evaluation of Specimen Types and Saliva Stabilization Solutions for SARS-CoV-2 Testing, Journal of Clinical Microbiology, 59(5):1-13.
Harry, 2021, Extraction-free RT-PCR to Detect SARS-CoV-2 Variants of Concern, Open Forum Infect Dis, 8(Suppl 1), pp. S89-S90.
International Search Report and Written Opinion issued in International Application No. PCT/US2022/36993, date of mailing: Nov. 2, 2022, 24 pages.
Narang, 1979, Improved phosphotriester method for the synthesis of gene fragments, Methods Enzymol 68:90-98.
Qui, 2021, SARS-CoV-2 viral load monitoring by extraction-free testing of saliva, medRxiv, 25 pages.
Rabe, 2020, SARS-CoV-2 detection using isothermal amplification and a rapid, inexpensive protocol for sample inactivation and purification, PNAS, 117(39):24450-24458.
Vogels, 2020, A simplified and felxible platform to enhance SARS-CoV-2 testing capacity, Med 2(3):263-280.
Zhong, 2011, Multiplex digital PCR: breaking the one target per color barrier of quantitative PCR, Lab Chip 11:2167-2174.
Smyrlaki et al.: "Massive and rapid COVID-19 testing is feasible by extraction-free SARS-cov-2 RT-PCR", Nature Communications, (2020), vol. 11, No. 1, pp. 1-12.
Bloom et al.: "Massively scaled-up testing for SARS-cov-2 RNA via next generation sequencing of pooled and barcoded nasal and saliva samples", Nature Biomedical Engineering, Nature Publishing Group UK, London, (2021), vol. 5, No. 7, pp. 657-665.
Kim et al.: "Comparison between Saliva and Nasopharyngeal Swab Specimens for Detection of Respiratory Viruses by Multiplex Reverse Transcription-PCR", Journal of Clinical Microbiology, (2017), vol. 55, No. 1, pp. 226-233.
Qiu et al.: "SARS-coV-2 viral load monitoring by extraction-free testing of saliva", medRxiv, (2021), pp. 1-25.

* cited by examiner

*Primary Examiner* — Agnieszka Boesen
(74) *Attorney, Agent, or Firm* — Thomas C. Meyers; Sullivan & Worcester LLP

(57) ABSTRACT

The invention provides compositions, devices, methods and kits allowing for rapid diagnosis of infectious diseases via extraction-free, direct PCR techniques using combined biological samples.

19 Claims, 6 Drawing Sheets

Vial

Saliva Collector

Swab

DEVICES AND METHODS FOR EXTRACTION-FREE PATHOGEN TESTING

TECHNICAL FIELD

The invention generally relates to diagnostic methods, and, more particularly, to compositions and methods for performing extraction-free pathogen testing and detection.

BACKGROUND

The rapid global spread of contagious diseases presents a major healthcare challenge. For example, the rapid spread of the severe acute respiratory syndrome coronavirus-2 (SARS-CoV-2), resulting in a global pandemic, has placed an emphasis on the criticality of rapid and early detection.

Current detection techniques for many infectious diseases involve the use of polymerase chain reaction (PCR). PCR is a technique used to selectively amplify a specific region of DNA of interest (the DNA target). For example, various real-time PCR assays (also referred to as quantitative PCR (qPCR)) for detecting SARS-CoV-2 RNA have been developed worldwide, with different targeted viral genes or regions.

While current PCR methods allow for the detection and diagnosis of infectious diseases, those methods suffer from drawbacks. One notable drawback is that current approaches rely on an initial step of isolating and purifying nucleic acids from a clinical sample as part of the viral testing protocol. The initial nucleic acid isolation and purification step (i.e., extraction step) required in conventional methods, prior to undergoing PCR, constitutes a major bottleneck in the diagnostic process, as it remains both manually laborious and expensive, and further increases the chances of accidental contamination and human error.

Furthermore, the efficacy of PCR-based tests for diagnosing SARS-CoV-2 can vary based on the type of sample analyzed (e.g., saliva or an anterior nares nasal swab), the timing of sample collection relative to the course of an infection, and even the behavior of subjects prior to sample collection. Recent analyses have shown that, for SARS-CoV-2, early in the course of an infection, upper respiratory samples have the highest concentration of viral particles, which declines after onset of symptoms. In contrast, lower respiratory samples have higher viral loads later in the course of the disease.

Other viral and non-viral pathogens (e.g., bacteria, fungi, etc.) are also amenable to detection via PCR and related processes. Moreover, certain pathogens are not stable in typical samples, such as saliva, which make detection of an intact pathogen difficult.

SUMMARY

The present invention provides compositions and methods for rapid, extraction-free detection and analysis of nucleic acid in saliva and respiratory mucosa.

Methods of the invention are applicable to the detection of any pathogen that is amenable to PCR amplification and includes viruses, such as influenza and SARS-CoV-2, as well as bacteria and other pathogens. In one aspect, the invention allows the combination of two different sample types in a single assay, thus allowing more accurate results during the entire course of an infection. For example, evidence has emerged that the abundance or clearance of SARS-CoV-2 or other respiratory viruses can vary in the nasal cavity versus saliva across individuals, or at different points of time during the course of the infection. Thus, unlike the methods of the invention, tests relying on a single specimen type can miss positive cases.

Further, it was recently discovered that for saliva-based tests, a test subject's behavior could hamper the ability of the tests to positively detect pathogen. For example, saliva samples collected well after a subject awoke, or after eating, drinking, or brushing teeth, provided lower positive detection rates for SARS-CoV-2. By taking two unique sample types, methods of the invention mitigate the effects a test subject's behavior may have on the accuracy of a test. Moreover, for respiratory infections, a combined saliva and respiratory mucosa sample, the invention allows successful detection of a virus using minimally-invasive sample collection.

In another aspect, the invention provides a stabilizing buffer that preserves pathogen in a sample. The buffer, described below, stabilizes both virus and bacteria for transport prior to detection of pathogen nucleic acid. In a preferred embodiment, a transport buffer as described herein is added to a liquid sample suspected of containing a pathogen. The sample is then transported to a laboratory for extraction and testing. Because buffer compositions disclosed herein preserve both viral and bacterial pathogens, multiple pathogen detection assays can be run in a single sample and/or sample types can be combined for multiplex pathogen analysis. The invention contemplates the use of any sample type, but preferably a liquid sample such as blood, sputum, saliva, nasal mucosa, cerebrospinal fluid, urine, pus, breast nipple aspirate, ascites, lymphatic fluid, sweat and lacrimal fluid is used.

In a first aspect, the invention provides compositions for processing a combined saliva and respiratory mucosa sample and providing usable nucleic acid for subsequent amplification and/or detection (for example, using next generation sequencing technologies), while eliminating the need for an initial nucleic acid extraction step. Compositions of the invention eliminate the need for pathogen transport media, which typically inhibit PCR. Compositions of the present invention include, for example, a unique buffer for sample transport and preparation that, when mixed with a sample of interest, is capable of preparing nucleic acid from the sample that is suitable for direct nucleic acid amplification and analysis without the need for initial nucleic acid extraction (i.e., isolation and purification of the nucleic acid).

In one aspect, the invention avoids conventional approaches for pathogen detection, which may include, for example, an RNA extraction step using industrial RNA extraction kits and techniques. Instead, sample testing using the methods of the invention is direct and avoids the extraction step. After the combined samples are provided in a unique buffer composition, nucleic acid samples may then be used for downstream qPCR, rtPCR, or NGS-based diagnostic testing. The invention is useful for the detection of DNA or RNA, as required for detection of a target nucleic acid.

In certain aspects, the present invention includes kits with all the necessary components to obtain a combined sample, which may preferably be saliva and mucosal samples. This may include providing patients with a kit. The subject can use the simple-to-use components of the kit, in the comfort of their home, to provide a sample. Using the proprietary buffer compositions disclosed herein, the sample can be adequately preserved and secured, such that it can be mailed to a laboratory for analysis.

For purposes of the invention, the target nucleic acid may be a human genomic sequence, a human transcript sequence, a pathogen sequence or a parasitic sequence.

In a preferred embodiment, compositions and methods of the present invention improve upon conventional testing and detection approaches by using a combined saliva and respiratory mucosa sample, while concurrently reducing the number of steps required for sample preparation and testing. In turn, the time required for testing is greatly reduced, resulting in faster turnaround times and delivery of results. Furthermore, because the methods of the invention test combined samples using a single assay, the present invention reduces the cost of labor and consumables, while further reducing cross contamination of samples as well as infections of the samples to operators.

In one aspect, the invention provides methods for detecting a viral infection. In some certain methods, the viral infection is a coronavirus, such as a severe acute respiratory syndrome coronavirus (e.g., SARS-CoV-2). However, it should be noted that methods of the present invention are useful for the detection other viral infections.

Methods include the steps of obtaining a combined saliva and respiratory mucosa sample from a patient. In certain aspects, obtaining the combined sample includes collecting saliva from a subject (e.g., via having patients spit into an appropriate collection vessel) and respiratory mucosa (collected via nasopharyngeal or throat swabs).

Preferred methods further include mixing the combined sample with an inventive buffer composition that is capable of preparing nucleic acid from the biological sample suitable for nucleic acid amplification without initial extraction of the nucleic acid. In other words, upon mixing of the biological sample with the buffer, specific components within the buffer allow for nucleic acid from the sample to be sufficiently prepared for subsequent nucleic acid analysis (i.e., amplification via PCR) without requiring the typical extraction (isolation and purification) step.

Buffer compositions used in the methods of the invention generally include nuclease-free water, an antifungal solution, an antibiotic solution, a ribonuclease inhibitor, a reducing agent solution and/or a Tris-Borate-EDTA buffer solution. In certain aspects, the buffer composition also serves as a transport medium, in which the combined sample, including any sample collection swab(s)m is immediately placed within an appropriate collection vessel containing the buffer composition.

Methods further include performing one or more PCR assays on the prepared nucleic acids to detect viral nucleic acid. Upon detection of the viral nucleic acid, a patient may be diagnosed as having been infected with a virus.

The step of performing PCR assays includes using viral nucleic acid specific primer-probe sets. In certain aspects, the viral nucleic acid specific primer-probe sets target one or more of the virus's N, ORF1ab, and E genes. In some embodiments, the step of performing the PCR assay includes using a primer-probe set specific to ribonuclease P (RNP). Extraction methods disclosed herein are also useful for detecting human genomic or RNA sequences, as methods are agnostic as to the source of nucleic acid.

In certain aspects, methods of the invention further include quantifying the viral nucleic acid. For example, performing the one or more PCR assays includes performing at least one of quantitative PCR (qPCR) and digital PCR (dPCR), which may include droplet digital PCR (ddPCR). In addition to diagnosing the patient as either having been or not been infected with the virus, the method may further include the step of determining the severity of the viral infection based on the viral nucleic acid quantity. In some embodiments, methods may further include the step of comparing viral nucleic acid quantities in a plurality of biological samples obtained from the patient at successive time points and determining disease progression based on increases or decreases in the viral nucleic acid quantities over time. Methods of the invention may further include predicting disease outcomes based on the identity or quantity of viral nucleic acid. Methods of the invention may also be used to inform a course of treatment or prognosis. For example, results can be used to determine an appropriate therapeutic or clinical procedure.

In another aspect, the invention provides for detection of bacteria using extraction-free buffer to preserve bacterial DNA and/or RNA for detection. The same buffer is useful for preservation of both virus and bacteria, thus allowing detection of viral and bacterial pathogens in the same sample or combination of samples. Thus, in one aspect the invention provides methods of stabilizing bacteria and/or virus in a biological sample for extraction-free testing via, for example, PCR. The invention therefore allows simultaneous detection of viral and bacterial samples. This allows for an "all-in-one" test for viral and bacterial sexually-transmitted infections (STI), such as *Chlamydia trachomatis* and *Neisseria* gonorrhea. In addition, because the buffers disclosed herein stabilize influenza virus as well as SARS viruses, a single test is used to detect influenza and, for example, SARS-CoV-2.

The present invention also provides methods for extraction-free analysis of nucleic acid. An exemplary method includes the steps of providing a vial and obtaining a saliva sample from a subject in the vial. The method further includes obtaining a respiratory mucosa swab sample from the subject. The method includes mixing the saliva sample and respiratory mucosa swab sample in the vial. Preferably, the combined sample is mixed in the vial with a preservation buffer composition, which includes, for example buffer nuclease-free water, an antifungal, an antibiotic, and a ribonuclease inhibitor. Thus, methods include directly amplifying nucleic acid in the buffer with primers specific to a target nucleic acid. Direct amplification occurs without a prior nucleic acid extraction step. After amplification, the method includes analyzing amplicons produced in said amplifying step to detect presence of one or more pathogen.

In certain aspects, a saliva sample is obtained from the subject using a saliva collection aid (SCA) or a funnel. The SCA may include the buffer composition, which is released into the vial. For example, the SCA may include the buffer composition in an internal pouch or compartment or in the lid, which releases the buffer composition into the vial. In certain aspects, the SCA or funnel includes a lid. The lid may include the buffer composition, which is released into the vial when the lid is closed. In certain aspects, the SCA or funnel is integrated with the vial. Alternatively, the SCA or funnel may be configured to couple to the vial during saliva collection. In certain aspects, the SCA or funnel is configured such that it can be reversibly coupled to the vial.

Preferably, a respiratory mucosa swab sample is obtained by swabbing a subject's anterior nares. In certain aspects, the swab used to obtain the respiratory mucosa sample is attached to a cap used to seal the vial. Sealing the vial with the cap may place the swab in the saliva sample, such that the saliva sample and the swab sample are combined.

The present invention also provides kits for performing the methods of quantifying the nucleic acids, including viral and/or bacterial nucleic acids, as disclosed herein. In certain aspects, a kit of the invention includes one or more vials, saliva collection aid and/or funnel; a buffer composition, such as a transport (preservation) buffer, primers for amplifying one or more target nucleic acid, and instructions for use.

DETAILED DESCRIPTION

Figure 1:
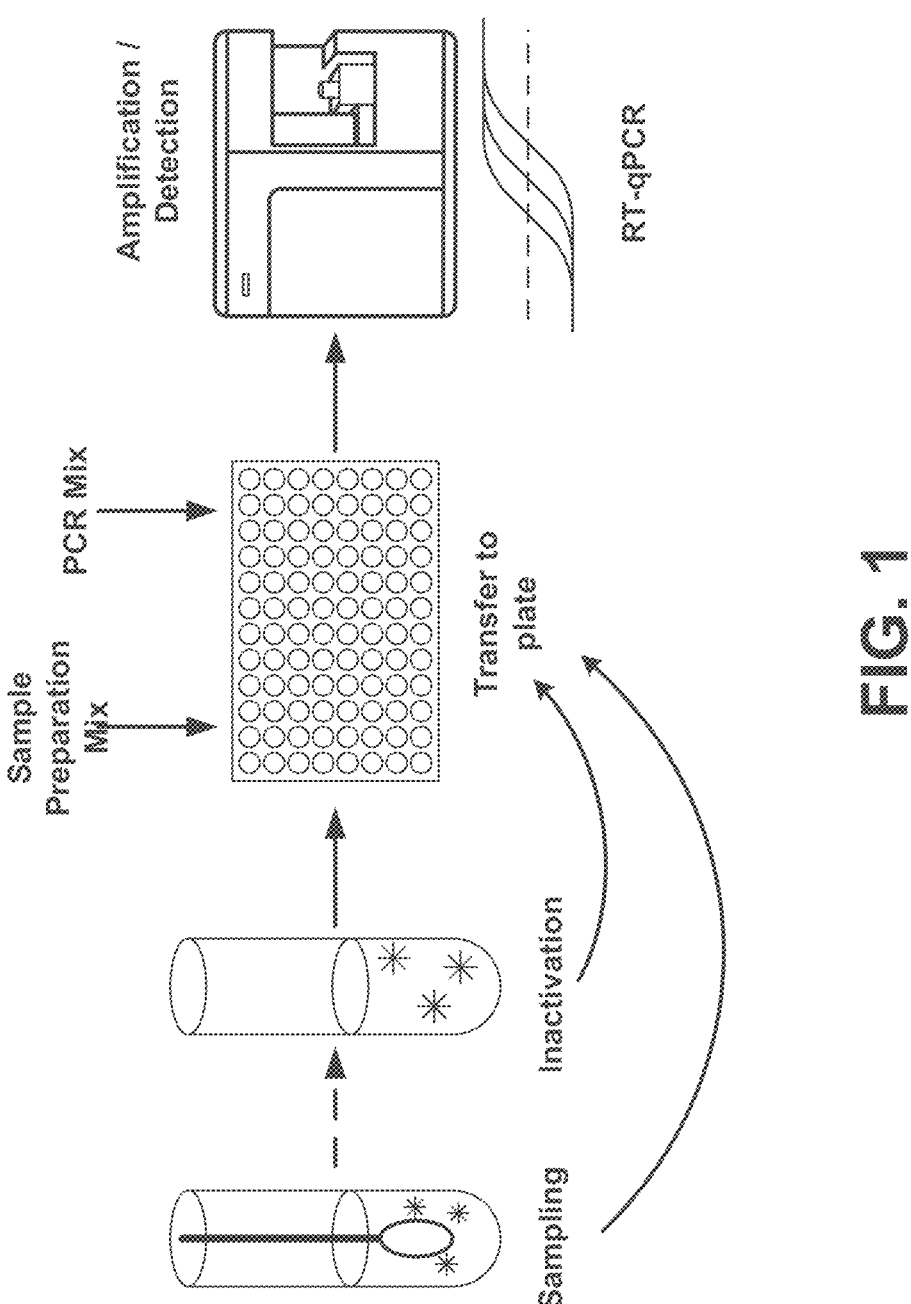
FIG. 1 shows a schematic overview of an extraction-free, real-time RT-qPCR test intended for the qualitative detection of nucleic acid from SARS-CoV-2 in biological specimens (spit or swab samples) collected and processed via unique buffer compositions of the present invention.

The present invention provides compositions, methods, and kits allowing for rapid diagnosis of infectious diseases via extraction-free, direct PCR techniques using combined samples obtained from two or more sources. The invention also provides a stabilizing buffer that allows extraction-free testing of pathogen nucleic acid and, in particular, multiple pathogens simultaneously from one or more sources. Thus, methods of the invention include methods for viral testing, bacterial testing, or combinations. Moreover, because buffers taught herein preserve samples, ranging from SARS to influenza to bacteria, samples can be transported without substantial loss of the target pathogen. Finally, methods of the invention allow analysis of the time course of infection as a pathogen moves from one location to another (e.g., an influenza or SARS virus moving from the nasal passage to the throat.

Compositions, methods, and kits of the invention may be used for processing a combined biological sample (e.g., saliva and respiratory mucosa) and providing usable DNA for subsequent PCR assays, while eliminating the need for an initial RNA extraction step. The present invention includes a unique buffer composition for sample transport and preparation that, when mixed with a sample of interest, is capable of preparing nucleic acid from the sample that is capable of being directly used for nucleic acid amplification and analysis without the need for initial nucleic acid extraction (i.e., isolation and purification of the nucleic acid). Accordingly, unlike prior approaches, which include an RNA extraction step using industrial RNA extraction kits and techniques, the direct combined sample testing of the present invention circumvents this process by omitting the extraction step. Instead, after clinical samples are provided in the unique buffer composition, pathogen may be inactivated either through heating or by direct lysis in the buffer. The inactivated samples can then be used for downstream qPCR diagnostic testing.

As a result, compositions, methods, and kits of the present invention improve upon conventional pathogen testing and detection approaches by reducing the number of steps required for sample preparation and testing. In turn, the time required for testing is greatly reduced, resulting in faster turnaround times and delivery of results. Furthermore, the present invention reduces the cost of labor and consumables, while further reducing cross contamination of samples as well as infections of the samples to operators. The efficiency and costs saving are magnified by using combined samples in accordance with the methods of the invention. Tests using combined samples require only a single assay to provide results. Moreover, as they are more sensitive and accurate compared with existing tests, they reduce the need to provide follow up tests due to ambiguous or false results.

It should be noted that the methods described herein may be used to diagnose a variety of contagious diseases, including microbial and viral. However, for the sake of simplicity and ease of description and example, the following describes methods for diagnosing SARS-CoV-2 via extraction-free direct PCR approaches.

SARS-CoV-2 is a virus recently identified as the cause of an outbreak of respiratory illness (referred to as coronavirus disease 2019 (COVID-19)) with an increasing number of patients with severe symptoms and deaths. Typically, with most respiratory viruses, people are thought to be most contagious when they are most symptomatic. With SARS-CoV-2, however, there have been reports of asymptomatic spread from infected individuals. SARS-CoV-2 testing efficacy is further complicated as analyses have shown that, early in the course of an infection, upper respiratory samples have the highest concentration of SARS-CoV-2 viral particles, which declines after onset of symptoms. In contrast, lower respiratory samples have higher viral loads later in the course of the disease. Accordingly, to monitor the presence of SARS-CoV-2 and to prevent its spread, it is crucial to detect infection as early and as fast as possible.

The methods of the present invention provide rapid detection of a viral infection (i.e., presence of the virus in a patient) by reducing the number of steps during sample preparation that are typically required with conventional viral detection methods relying on PCR assays. Moreover, by using combined samples, testing can be performed concurrently on samples obtained from locations that harbor high concentrations of viral particles at different points in time during the course of an infection.

In general, the workflow comprises obtaining a combined biological sample from an individual suspected of being infected. The method of sample collection, as well as the type of samples collected, may depend on the specific viral disease to be tested. For example, the combined samples used in the invention may include one or more body fluid and may be collected in any clinically-acceptable manner. The fluid sample is generally collected from a patient either exhibiting signs or symptoms of a viral disease, or suspected of having contracted the viral disease due to interaction with others that have tested positive for the disease.

A body fluid may be a liquid material derived from, for example, a human or other mammal. Such body fluids include, but are not limited to, mucous, blood, plasma, serum, serum derivatives, bile, blood, maternal blood, phlegm, saliva, sputum, sweat, amniotic fluid, menstrual fluid, mammary fluid, follicular fluid of the ovary, fallopian tube fluid, peritoneal fluid, urine, semen, and cerebrospinal fluid (CSF), such as lumbar or ventricular CS. Combined samples may also include media containing cells or biological material. Combined samples may also include a blood clot, for example, a blood clot that has been obtained from whole blood after the serum has been removed. In certain aspects, the combined sample includes two or more of saliva, respiratory mucosa, blood, or semen collected from the subject.

For SARS-CoV-2, a combined sample generally includes saliva combined with samples collected via a nasopharyngeal or throat swab. Next, the combined sample is prepared for subsequent analysis. Preparation of the combined sample includes mixing the sample with a buffer composition capable of preparing nucleic acid from the biological sample suitable for nucleic acid amplification without initial extraction of the nucleic acid. In certain aspects, a saliva sample is collected, and a swab placed in the sample for sample preparation. The swab may be squeezed or agitated to extract the sample and mix it with the other portion of the combined sample (e.g., saliva).

As previously noted, current viral testing approaches rely on an initial step of isolating and purifying nucleic acids from a clinical sample as part of the viral testing protocol. For example, the application of qPCR for the relative quantification of an RNA of interest is preceded by: (1) the isolation and purification of total RNA from the sample; (2) elution and possible concentration of the material; and (3) the use of purified RNA in a reverse-transcription (RT) reaction resulting in complementary DNA (cDNA), which is then utilized for the qPCR reaction. The initial nucleic acid isolation and purification step (i.e., extraction step) required in current methods, prior to undergoing PCR, constitutes a major bottleneck in the diagnostic process, as it remains both manually laborious and expensive, and further increases the chances of accidental contamination and human error.

The present invention provides compositions for processing combined samples and providing usable DNA for subsequent PCR assays, while eliminating the need for an initial RNA extraction step. For example, a unique buffer composition is used for sample preparation such that, when mixed with the biological sample, it is capable of preparing nucleic acid from the sample which is able to be being directly used for nucleic acid amplification and analysis without the need for initial nucleic acid extraction (i.e., isolation and purification of the nucleic acid).

When there is an insufficient amount of nucleic acid for analysis, a common technique used to increase the amount includes amplifying the nucleic acid. Amplification refers to production of additional copies of a nucleic acid sequence and is generally carried out using polymerase chain reaction or other technologies well known in the art (e.g., Dieffenbach, PCR Primer, a Laboratory Manual, 1995, Cold Spring Harbor Press, Plainview, NY). Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. Amplification or sequencing adapters or barcodes, or a combination thereof, may be attached to the fragmented nucleic acid. Such molecules may be commercially obtained, such as from Integrated DNA Technologies (Coralville, IA). In certain embodiments, such sequences are attached to the template nucleic acid molecule with an enzyme such as a ligase. Suitable ligases include T4 DNA ligase and T4 RNA ligase, available commercially from New England Biolabs (Ipswich, MA). The ligation may be blunt ended or via use of complementary overhanging ends.

For example, DNA may be synthesized from viral RNA associated with the virus of interest (if present) within the biological sample, via reverse transcription, to thereby produce complementary DNA (cDNA). As generally understood, reverse transcriptases (RTs) use an RNA template and a short primer complementary to the 3' end of the RNA to direct the synthesis of the first strand cDNA, which can be used directly as a template for amplification (via PCR). This combination of reverse transcription and PCR (RT-PCR) allows the detection of low abundance RNAs in a sample, and production of the corresponding cDNA, thereby facilitating the cloning of low copy genes. Alternatively, the first-strand cDNA can be made double-stranded using DNA Polymerase I and DNA Ligase. Many RTs are available from commercial suppliers. The use of engineered RTs improves the efficiency of full-length product formation, ensuring the copying of the 5' end of the mRNA transcript is complete, and enabling the propagation and characterization of a faithful DNA copy of an RNA sequence. The use of the more thermostable RTs, where reactions are performed at higher temperatures, can be very helpful when dealing with RNA that contains high amounts of secondary structure.

Digital polymerase chain reaction (dPCR) is a refinement of conventional polymerase chain reaction methods that can be used to directly quantify and clonally amplify nucleic acids strands including DNA, cDNA, or RNA. In dPCR a sample is separated into a large number of partitions and the reaction is carried out in each partition individually, thereby permitting sensitive quantification of target DNA through fluorescence analysis in each partition as opposed to a single value for the entire sample as found in standard PCR techniques.

Droplet Digital PCR (ddPCR) is a method of dPCR wherein the aforementioned partitions consist of nanoliter-sized water-oil emulsion droplets in which PCR reactions and fluorescence detection can be performed using, for example, droplet flow cytometry. The methods for creating and reading droplets for ddPCR have been described in detail elsewhere (see Zhong et al., 'Multiplex digital PCR: breaking the one target per color barrier of quantitative PCR', Lab Chip, 11:2167-2174, 2011), but in essence each droplet is like a separate reaction well and, after thermal cycling, the fluorescence intensities of each individual droplet were read out in a flow-through instrument like a flow cytometer that recorded the peak fluorescence intensities.

While compositions and methods of the invention may be used to detect nucleic acid specific to any virus, in preferred embodiments, SARS-CoV-2 is the detection target. Exemplary primers and probes for the detection of SARS-CoV-2 have been disclosed by the Chinese CDC (targeting the N and ORF1ab genes) and the WHO (targeting the E gene) and are provided in Tao S, et al., 2020 and Dong, I et al. 2020. Compositions and methods of the invention for the detection of COVID-19 infection using ddPCR of combined saliva and nasopharyngeal samples contemplate using the same primers and probes discussed therein. Furthermore, in some embodiments, the step of performing the one or more PCR assays includes using a primer-probe set specific to ribonuclease P (RNP).

In addition to diagnosing an individual as having been infected with the virus, inventive methods may further include the step of determining the severity of the viral infection based on the viral nucleic acid quantity in the combined sample. For example, methods of the invention are useful to assess viral load, which can be directly correlated with disease severity and/or progression. In some embodiments, methods may further include the step of comparing viral nucleic acid quantities in a plurality of combined biological samples obtained from the patient at successive time points and determining disease progression based on increases or decreases in the viral nucleic acid quantities over time. Methods of the invention can also be used to predict disease outcomes and/or severity based on the viral nucleic acid quantity. The disease outcomes are selected from one or more of intubation, ICU admission, discharge, time until intubation, time until discharge, and death.

FIG. 1 shows a schematic overview of an extraction-free, real-time RT-qPCR test intended for the qualitative detection of nucleic acid from SARS-CoV-2 in combined biological specimens (spit and swab samples) collected and processed via unique buffer compositions of the present invention. In certain aspects, to collect saliva a patient will simply spit in an acceptable vessel. A nasopharyngeal swab is used for the collection of respiratory mucosa and then placed within the vessel containing the saliva. The swab can be squeezed or agitated to extract the mucosa sample and mix it with the saliva. The vessel may include a unique buffer composition of the invention, or it may be added after the combined sample. In certain aspects, the buffer composition can be used for sample preparation and/or a transport medium.

After collecting the combined samples and providing them with the unique buffer composition, viral particles may be inactivated either through heating or by direct lysis in the buffer. The inactivated samples can then be used for downstream qPCR diagnostic testing without the need for the additional RNA extraction step (isolation and purification) that conventional approaches rely on.

Rather, the prepared sample may be transferred to a PCR-plate (96/384-well) format in which cDNA synthesis by RT and detection by qPCR may take place. Accordingly, unlike the widely used approach, which includes an RNA extraction step using industrial RNA extraction kits, direct sample testing circumvents this process by omitting extraction.

Figure 4:
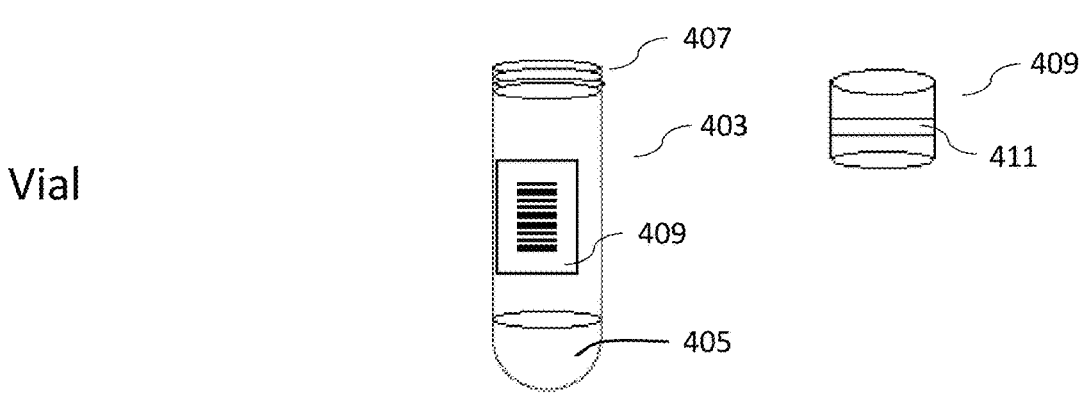
FIG. 4 shows select components used in methods of the disclosure and provided in certain kits of the invention.
Figure 4:
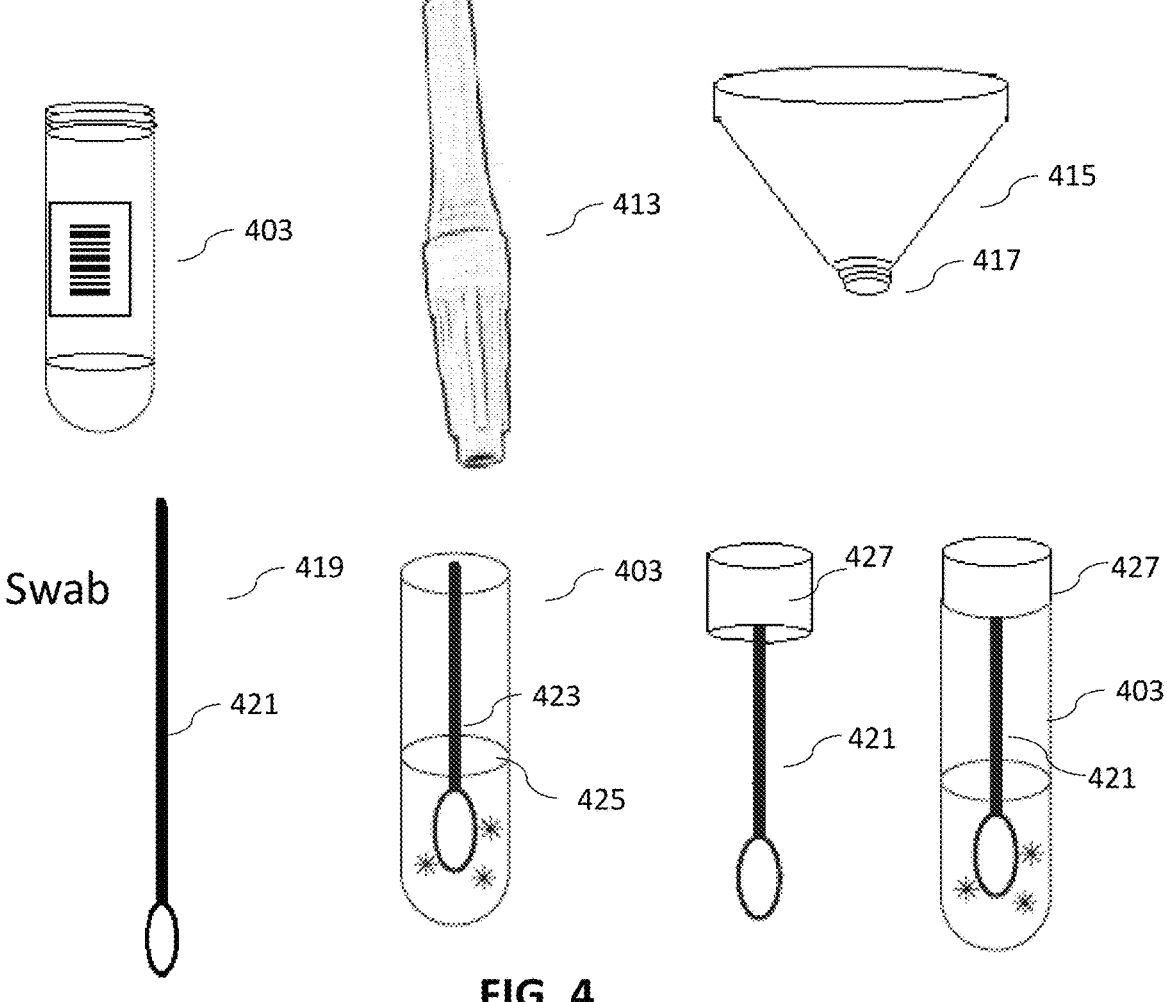

FIG. 4 shows certain components used in the methods of the invention. In certain aspects, one or more of the components can be provided as part of a diagnostic kit, along with instructions for use. As shown, the methods and kits of the invention may include a vial 403. In certain aspects, the vial is provided with a buffer composition 405. The buffer composition is for example, a viral transport buffer as disclosed herein. In certain kits and methods of the invention, the vial 403 is provided pre-filled with the buffer composition 405. Alternatively, the buffer composition is added to the vial before or after sample collection.

Preferably, the vial is at least 1.5 mL such that it can accommodate a saliva sample, swab sample, and any buffer composition. For example, samples may be collected in a centrifuge tube, such as the screw cap cryovial. An exemplary vial includes a barcode 407, which can be used to track individual vials and/or collected samples. Vials useful in connection with the presently disclosed invention include, polypropylene cryovials, such as the NEST Scientific USA (NJ, USA) 1.9 mL 2D Barcoded cryovials.

In certain aspects, the vial includes a thread 407 or other means for affixing a cap, lid, funnel, and/or saliva collection aid. In certain aspects, the thread 407 or other affixing means is used to affix a cap 409 to the vial to seal the sample for transport and/or storage. In certain aspects, the cap 409 includes a compartment or pouch 411. Affixing the cap 409 on the vial causes the compartment to perforate or otherwise release a buffer composition from inside the compartment or pouch 411 into the vial 403.

In certain aspects, methods and kits of the invention include a means for collecting a saliva sample from a subject. In some methods and kits, the subject merely spits into the provided, sterile vial 403. Alternatively, a saliva collection aid (SCA) 413 or funnel 415 is provided to facilitate saliva collection. Exemplary saliva collection aids include, for example, those produced by Salimetrics, LLC (Carlsbad, CA). Exemplary funnels include the NEST Scientific USA USP VI Polypropylene Funnels. The saliva collection aid 413 or funnel 415 may include a means, such as screw threads 417, for coupling the SCA/funnel to the vial during saliva collection. Alternatively, the funnel or SCA is integrated into the vial to form a single unit.

Preferably, when provided as a diagnostic kit, the SCA/funnel is pre-attached to the vial. The SCA/funnel may include a means for sealing the combined sample, such as a lid or cap. Alternatively, the SCA/funnel can be removed, e.g., through a thread and screw attachment means. Once removed, the SCA/funnel can be replaced by a cap or lid for sealing the combined sample in the vial.

An SCA 413 or funnel 415 may include a pouch or compartment that includes a buffer composition, such as a viral transport buffer as disclosed herein. The pouch or compartment may release the buffer during saliva collection. For example, the pouch or compartment may be integrated within a lid or cap for the funnel/SCA, such as that used with in the OME-505 collection kit, DNA Genetek, Inc., Ottawa, Canada. Closing the lid or cap causes a compartment to perforate, thereby releasing the buffer into the vial with the saliva sample.

Methods and kits of the invention also include or use a swab for collecting a respiratory mucosa sample. In certain aspects, the swab 419 includes a handle 421, which is held while a sample is being obtained from a subject. The handle 421 may include a break point. After the sample is obtained, the handle is snapped at the break point, which shortens the length of the handle. The swab with shortened handle 423 is thus short enough to fit within the vial 403. As shown, the level 425 of the saliva and/or buffer in the vial is sufficient to cover the swab. However, the level 425 of the saliva/buffer need not cover the swab. Rather, it is only necessary that the saliva/buffer are in an adequate quantity such that and swab and saliva sample can be mixed in the vial.

Alternatively or additionally, the swab 421 is coupled to a cap 427. The cap 427 can be coupled to the vial 403 after sample collection to seal the sample for transport, storage, and/or processing. As shown, when the cap 427 is affixed to the vial 403, the swab is positioned within the saliva/buffer in the vial.

In preferred aspects, the buffer composition is provided in a pre-filled vial or as part of another component of the kit, e.g., a cap as described herein. By providing the buffer in a pre-measured volume in a manner than can be easily added to the sample by a subject, exemplary kits of the invention allow a subject to provide a sample at home. By adding the pre-measured, novel viral transport buffer compositions of the invention to the combined sample, the subject can provide the sample at home or any other convenient location and send it via post to a laboratory for analysis.

Figure 5:
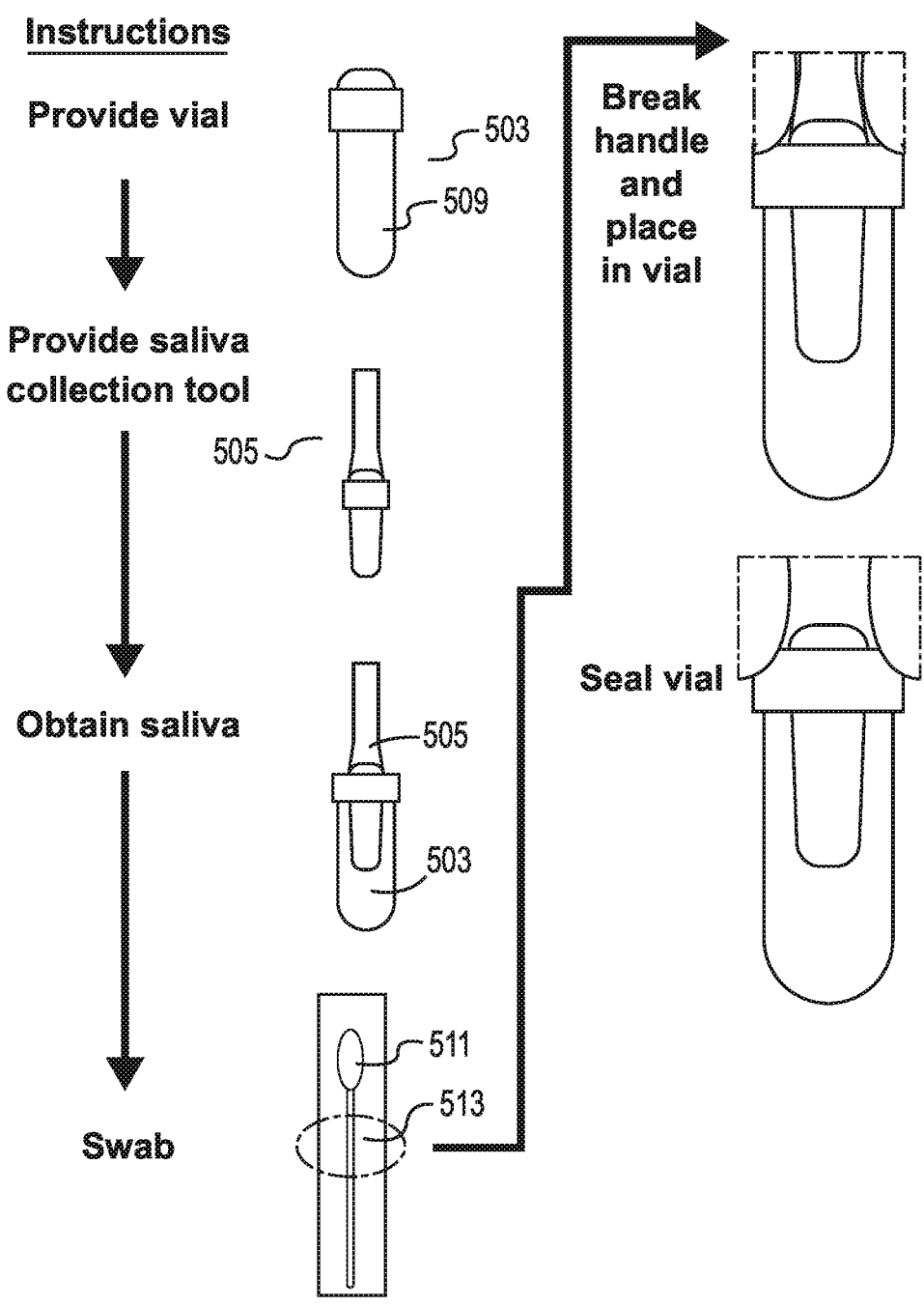
FIG. 5 shows select components of a kit of the invention for detecting a target nucleic acid in a combined sample.

FIG. 5 details select components of a kit of the invention used to detect a target nucleic acid (e.g., one indicative of a viral infection) in a sample. The kit includes instructions, which include the steps necessary to obtain a combined sample. The instructions outline that a vial 503 is provided to a subject along with a saliva collection tool, such as a saliva collection aid 505. As shown, in certain kits of the invention, the vial 503 comes pre-filled with a viral transport buffer 509, as described herein.

In the exemplary kit, the subject uses the provided saliva collection aid 505 to provide a saliva sample to the vial. As shown, the saliva collection aid 505 is shaped to fit securely in the opening of the vial 503 to facilitate sample collection.

The kit also includes a swab 511, which is used to swab the subject's anterior nares. The handle of the swab includes a break point 513. After the swab is used to obtain a sample, the handle is snapped at the break point. The shortened swab is placed into the vial with the saliva sample and buffer. The vial is then sealed with a cap for storage or transport. In certain aspects, the kit includes materials for a subject to mail the combined sample to a lab for analysis.

In certain aspects, the kit includes one or more primers, at least one of which is used for amplification and/or detection of a target nucleic acid in the sample.

Figure 6:
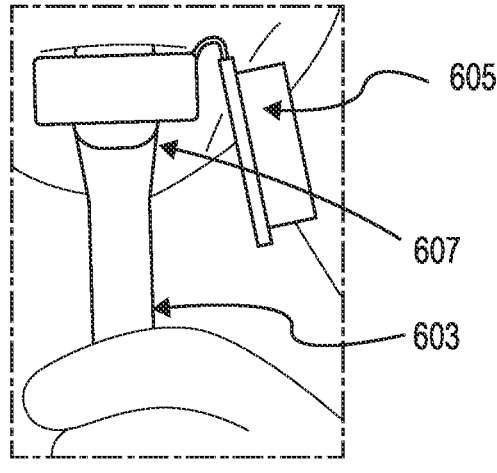
FIG. 6 shows select components of a kit of the invention for detecting a target nucleic acid in a combined sample.
Figure 6:
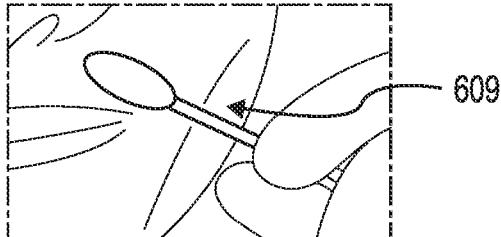
Figure 6:
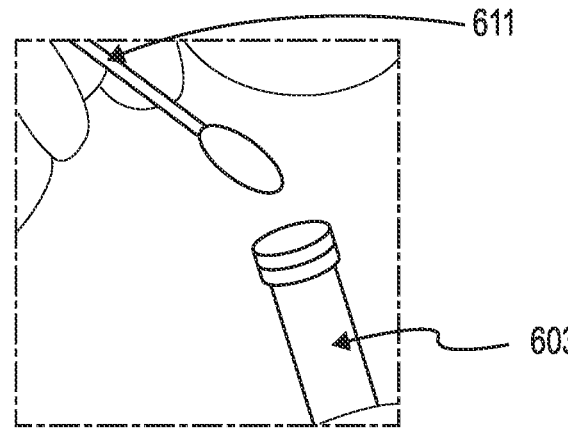

FIG. 6 details select components of a kit of the invention used to detect a target nucleic acid (e.g., one indicative of a viral infection) in a sample. The kit includes instructions, which include the steps necessary to obtain a combined sample. The instructions outline that a vial 603 is provided to a subject. The kit comes with a saliva collection aid 605 that can be coupled securely to the vial 603. Preferably, the kit comes with the saliva collection aid 605 pre-coupled to the vial 603. The saliva collection aid 605 includes a cap 607. When the saliva sample is provided into the vial, the cap 607 is closed over the saliva collection aid 605. Closing the cap 607 causes a compartment in the cap to rupture and flow a viral transport buffer into the vial 603, which contains the saliva sample.

The kit also includes a swab 609, which is used to swab the subject's anterior nares. As shown, the swab is affixed to a sealing cap 611. When the swab sample is obtained, the swab 609 is placed into the vial and the cap secured to the vial 603 using screw threads. By securing the sealing cap 611 to the vial 603, the swab sample is positioned within the saliva and buffer contained within the vial.

Figure 2:
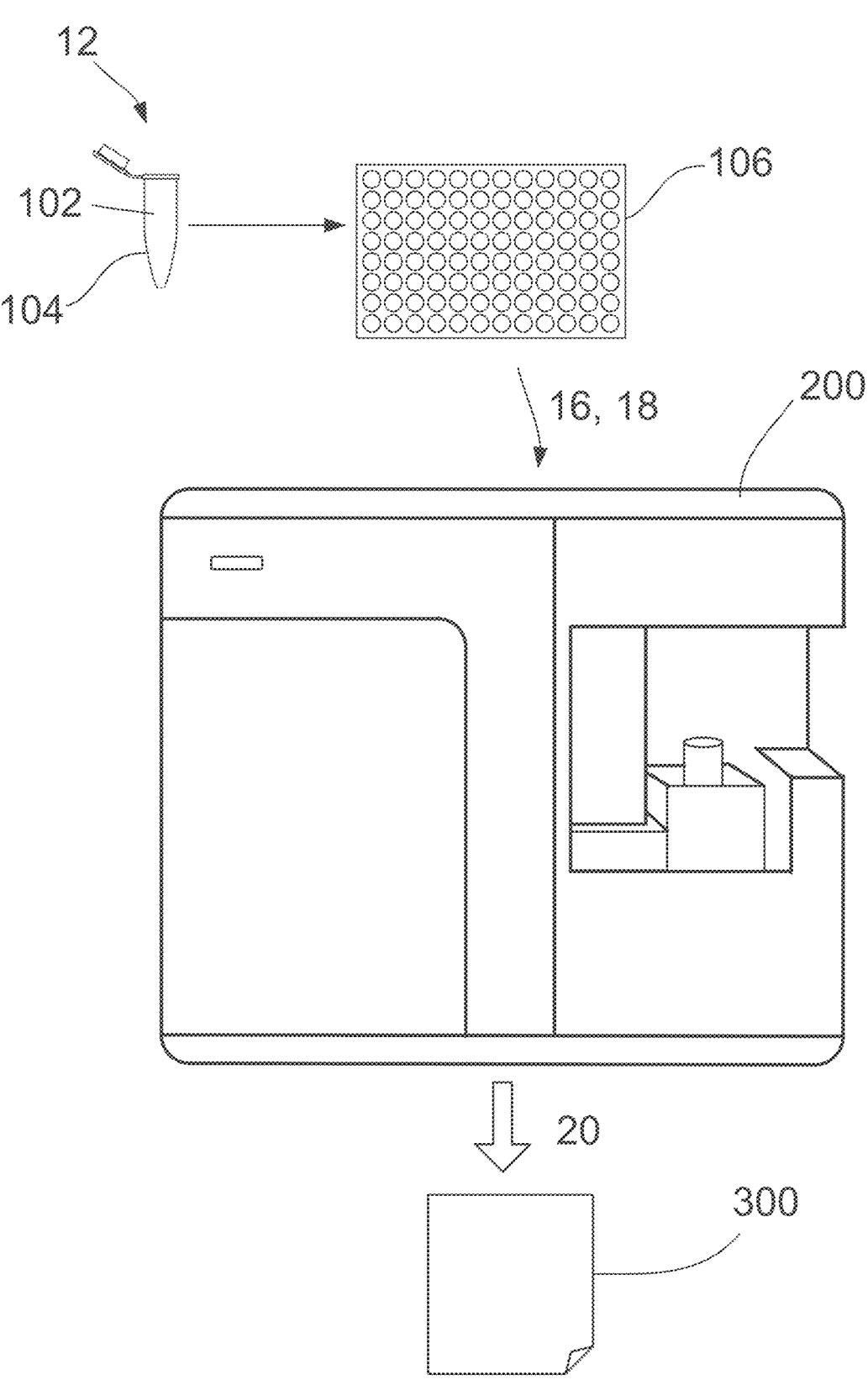
FIG. 2 shows a sample from a patient suspected of having a viral infection and loading of the sample into an instrument capable of performing one or more assays on the sample to determine whether viral nucleic acid associated with the viral infection is present.

FIG. 2 shows a combined sample 102 (e.g., saliva and respiratory mucosa) that has been collected from a patient suspected of having a viral infection and loading of the sample into an instrument 200 capable of performing one or more assays on the sample to determine whether viral nucleic acid associated with the viral infection is present. As will be described in greater detail herein, the combined sample 102 (saliva and respiratory mucosa) may be contained within a suitable container 104 that is obtained (operation 12 from a patient suspected of having a viral infection (or having been in close contact with one or more persons having or suspected of having the viral infection).

For example, combined samples may be collected and stored in their own container, such as a centrifuge tube such as the screw cap cryovial. Preferably a 1.9 ml cryovial with screw cap is used. A funnel or saliva collection aid is used to facilitate saliva collection, and a nasal swab with a proximal breakpoint is used, which allows the swab to be inserted into the tube after use. The advantage of using the same tube for both saliva and nasal swab is to facilitate downstream sample accessioning, automation using, for example, a decapper. The screw cap is important to prevent contamination. The standard size of cryovial is allow direct sample storage without additional sample transfer.

FIG. 2 further illustrates loading of the combined sample 102 into a PCR-plate 106, in which sample preparation may take place (introduction of the sample to the unique buffer and/or PCR mix), at which point the plate 106 may then be introduced into an instrument 200 capable of performing one or more PCR assays on the sample 102 to determine whether viral nucleic acid associated with the virus is present. In particular, the instrument 200 may be configured to provide any one of the prior steps of method, including, but not limited to, detection of viral RNA, reverse transcribing of RNA to produce cDNA, amplification of cDNA (operation 16), analysis of data from the amplification step (operation 18), and generation of a report 300 providing information related to the virus evaluation (operation 20).

Accordingly, the instrument 200 is generally configured to detect, sequence, and/or count the target nucleic acid(s) or resulting fragments. In this instance, where a plurality of fragments is present or expected, the fragment may be quantified, e.g., by qPCR. The resulting report 300 may include the specific data associated with the assay, including, for example, patient data (i.e., background information, attributes and characteristics, medical history, tracing information, etc.), test data, including whether the sample tested positive or negative for the virus, and, if positive, further metrics, including disease progression and predicted disease outcome.

Saliva and Nasal Swab Examples

The following examples provide exemplary protocols for detection of viral nucleic acid in accordance with methods of the present invention. A combined biological sample is obtained that includes sample from at least two location of a subject, e.g., a combined saliva and respiratory mucosa sample. Although the following examples highlight combined saliva and respiratory mucosa samples, other combined samples are included within the scope of the invention.

For example, combined samples as used herein may include combinations of one or more different body fluids. Exemplary body fluids include, but are not limited to, mucous, blood, plasma, respiratory mucosa, serum, serum derivatives, bile, blood, maternal blood, phlegm, saliva, sputum, sweat, amniotic fluid, menstrual fluid, mammary fluid, follicular fluid of the ovary, fallopian tube fluid, peritoneal fluid, urine, semen, and cerebrospinal fluid (CSF), such as lumbar or ventricular CS. A combined sample may also include a sample that is a media containing cells or biological material. A combined sample may also include a blood clot, for example, a blood clot that has been obtained from whole blood after the serum has been removed.

Further, as shown in the examples that follow, the portions of the combined sample can be obtained using a variety of techniques, such as through the use of swabs and/or direct body fluid collection. For many respiratory infections, a biological sample is generally collected via a nasal or throat swab, or, in some cases, saliva. In other examples, the sample may include an aerosol sample or droplets obtained in air or, more preferably, via the expulsion of droplets with a cough or sneeze.

Example 1

On-Site Combined Saliva and Nasal Swab (Anterior Nares) Sample Collection:

Saliva samples are collected from individuals by, for example, having them spit into a provided sterile container.

Saliva collection devices include, for example, a Nest 1.9 ml cryogenic vial (or "Nest tube") with screw cap (externally threaded) with a pre-printed 10-digit one-dimension barcode on the side and a laser-etched DATAMATRIX two-dimension code at the bottom will be used as the container of the saliva sample. A saliva collection support funnel (Nest) may be used in tandem with the Nest vial.

Nasal swab collection devices include, for example, an oral/Nares swab by Nest that is used to swab the patient's anterior nares. The swab with a respiratory mucosa sample is placed with its swab head facing downward inside the Nest tube containing the patient's saliva sample. The swab head may be agitated or squeezed to release the sample from the swab and/or combine the saliva sample with that of the swab.

The nasal swab (anterior nares) should be collected under the supervision of a trained healthcare worker designated by the organization overseeing the collection site. The healthcare worker supervising the collection should clean hands with alcohol-based sanitizer or fragrance-free soap and water and don appropriate PPE (gown, gloves, face mask, and/or face shield). Before collection, patients are provided instructional materials such as this one recommended by the FDA (https://tinyurl.com/nasalswab1-2). The healthcare worker ensures all patient information, including name, date of birth, and additional information required by state reporting rules, is filled out properly before collection. The healthcare worker then asks the patient to review a study consent form to opt in or out of the study (provided by Ovation). Lastly, the healthcare worker will scan a pre-printed barcode label to tie it to the patient information that is already collected, then place the label on the Nest tube that will be used by the patient.

The healthcare worker removes the cap of the Nest tube, directs the patient to swab their anterior nares ten times, and breaks the swab inside the tube at the proximal breakpoint. The healthcare worker will replace the cap of the Nest tube and make sure it is securely tightened. If there is any sample spill during the collection process, the healthcare worker will use an alcohol wipe or equivalent to wipe the outside of the tube to prevent contamination. The sample will then be placed in an individual bag under room temperature before being transported to the lab.

The healthcare worker supervising the swab sample collection should use alcohol-based hand sanitizer after handling each patient's sample.

Combined Sample Receiving and Accessioning in Lab:

The combined samples are transported to the lab. Samples are removed from bags and visually examined by the accessioning supervisor at the receipt desk for any leakage or damage. Samples passed the pre-screening step by the supervisor are moved to the desktop used by the accessioning team. Samples failed the pre-screening step are set aside for further investigation. Accessioners will scan the barcodes on the Nest tubes and examine patient information and consent status shown on a computer screen via a laboratory information management system (LIMS). Tubes with complete patient information in the LIMS and have no leakage (i.e., qualified samples), are placed in a bar-coded 48-format rack. The positions of the samples in the rack should match assigned positions in the LIMS. Disqualified samples are placed in another bar-coded 48-format rack and set aside for further investigation by the accessioning supervisor. The rack of samples may then be placed on a platform rocker in hold position @ 60 rpm until a medical lab scientist (MLS) from the sample preparation team fetches the samples.

Reaction Buffer:

As part of sample preparation, the combined sample is mixed with a unique buffer composition prepared specifically for the combined saliva and respiratory mucosa sample (referred to herein as a Combined Saliva\Mucosa Preparation Buffer). Preparation of the Saliva\Mucosa Preparation Buffer includes use of at least the following equipment: Biosafety cabinet or laminar flow hood (workspace capable of maintaining an aseptic environment); individual, sterile wrapped pipettes, pipette tips, such as 10 and 25 mL; pipette aid; pipettor, 1 mL or 200 μL and corresponding tips; and 50 ml sterile, nuclease-free Falcon tubes. An exemplary Saliva\Mucosa Preparation Buffer comprises the following reagents/components:

0.5 M Bond-Breaker TCEP solution, (Tris(2-carboxy-ethyl)phosphine hydrochloride, neutral pH), Sterile, DNase-, RNase- and Protease-Free grade, ThermoFisher Scientific, catalog number 77720, 5 mL;

RNase inhibitor, human placenta, 40,000 units/ml, Sterile, DNase-, RNase-Free grade, New England Biolabs, catalog number M0307L, 10,000 units, 250 ul/tube;

Amphotericin B solution, 250 μg/ml in deionized water, sterile, Sigma-Aldrich, catalog number A2942, 100 ml (or similar antifungal at an appropriate concentration to prevent fungal contamination and growth);

Penicillin-Streptomycin Solution, 100×, a mix of Penicillin (10,000 IU) and Streptomycin (10,000 μg/ml) in a 100-fold working concentration, Sterile, Corning, catalog number 30-002-CI (or similar antibiotics at an appropriate concentration to prevent bacteria contamination and growth;

Nuclease-free water, Sterile, Millipore/Sigma, W4502, DNase-, RNase- and Protease-Free grade; and Disinfectant, such as 70% ethanol.

Preparation the Saliva\Mucosa Preparation Buffer is in accordance with standard biological and/or clinical laboratory practices and procedures and is performed in a biosafety cabinet or laminar flow hood.

Preparation of the ingredients includes at least the following steps: clean work surface with appropriate disinfectant; disinfect reagent bottles prior to placing on work surface; aliquot nuclease-free water, 40 mL in 50 mL sterile Falcon tube, store at RT; aliquot Amphotericin B 4 ml/tube (in 5 ml sterile corning tube), store at −20 C; aliquot Penicillin/Streptomycin, 1 ml/tube (in sterile Eppendorf tubes), store at −20 C; and record lot information and preparation in a laboratory-controlled notebook.

Preparation of the Saliva\Mucosa Preparation Buffer includes at least the following steps:

1. Clean work surface with appropriate disinfectant;

2. Disinfect reagent bottles (aliquot, except RNase inhibitor) prior to placing on work surface;

3. For example, to prepare 5 mL buffer (for 1000 tests):

3.1. in a 15 mL sterile falcon tube, add 4.3 mL nuclease-free water;

3.2. add 400 uL TCEP;

3.3. using a sterile pipette, add 50 ul of RNase inhibitor;

3.4 thaw a tube of Amphotericin and a tube of Penicillin/Streptomycin, using a sterile pipette, aseptically add 200 uL of Amphotericin and 50 uL of Penicillin/Streptomycin to the 15 mL falcon tube;

4. Record lot information and preparation in a laboratory-controlled notebook;

5. Assign laboratory appropriate identification (e.g. lot number);

6. Cap the tube securely and mix thoroughly by inverting the tube;

7. Withdraw 100 ul of medium for QC sample;

8. Label the bottle as:

Saliva/Mucosa Reaction BUFFER

Lab ID: (Insert laboratory appropriate identification, such as STB1 as Summit Buffer 1)

DOM: (Insert current date of manufacture)

Expires: (Insert date 1 month after manufacture date)

Store at 2-8 C

9. Store at 2-8 C, add 5 ul/each test together with 30 uL of the combined saliva and respiratory mucosa sample and 5 uL proteinase K when performing FAST testing; and 10. Perform sterility check.

Example 2

Combined Saliva/Mucosa Sample Preparation:

An MLS from the sample preparation team will fetch the racks of accessioned samples on the rocker and bring them into the sample preparation room to prepare them for testing. They will bring prepared 96-well Sample Prep Plate (SPP) containing 10 μL/well of a Sample Prep Mix (SPM). The SPM contains the Saliva\Mucosa Preparation Buffer and a protease (Proteinase K). In particular, the 96-well SPP contains 10 μL SPM (5 μL Saliva\Mucosa Preparation Buffer and 5 μL Proteinase K (Promega))/well, dispensed into each well using a multichannel equalizer or Viaflow (Integra). The combined samples are decapped with a semi-automated 6-channel decapper (Brooks) or automated 48-format decapper (Brooks) inside the biosafety cabinets. Caps will be temporarily placed on the cap carrier rack when using the 6-channel decapper. Approximately 30 μL of the combined are transferred from the tubes in the 48-well rack using the E1-ClipTip electronic multichannel (8-channels) equalizer to the 96-well SPP containing the 10 μL SPM and pipetting well. Two 48-well racks of samples will fill one 96-well SPP. Samples are recapped (6 at a time if using the 6-channel decapper or 48 at a time if using the automated 48-format decapper). The combined saliva/mucosa samples and SPM are mixed well by placing the plates on the digital microplate shaker @ 500 RPM for 1 minute. The plate is placed on the miniAmp 96-well PCR instrument at 95° C. for 5 minutes, and 4° C. on hold. The entire racks of samples are then brought to the temporary sample storage area. Any of the samples that require repeat testing will be identified from the temporary sample storage area. Repeat testing is only allowed one time. If failed, request a new sample. Store left-over samples in −80° C. for future use.

PCR Reagent Preparation and Plate Setup (Combined Saliva/Mucosa Sample):

A plate containing a PCR master mix (herein referred to as a PCR Master Mix Plate (PMMP), includes 12.5 μL of PCR master mix dispensed into each well of the plate using a multichannel equalizer or Viaflow (Integra) on to a 96- or 384-well plate. The PCR master mix is composed of 10 μL Luna Universal Probe One-Step Reaction Mix, 1 μL Luna Warmstart RT enzyme Mix, and 1.5 μL of N1/RNP primer/probe. The 1.5 μL N1/RNP primer/probe will be made as: 6.7 μM working stocks of the N1 and RNP primers and 1.7 μM FAM-labeled N1 and ATTO-647 labeled RNP probe by adding 50.25 μL of each 100 μM primers and probe stock to 524 μL IDTE buffer (pH7.5).

The MLS in the molecular team will place a 96- or a 384-well PMMP into their individual PCR workstation and add 7.5 μL of treated combined saliva and respiratory mucosa sample from the Combined Saliva/Mucosa Sample Preparation Step to each designated well of the PMMP. The treated saliva sample is then mixed with the PCR master mix by pipetting, taking care to avoid introducing bubbles. The MLS then adds 7.5 μL of positive control (IDT synthetic 2019-SARS-CoV-N control, 4000 copies/uL), and negative control (IDT Hs-RPP30 control, 4000 copies/μL) for SARS-CoV-2, and no-template control (NTC—water) to designated PCR wells for the controls (1 positive control, 1 negative control, and NTC per plate) and mixes by pipetting, avoiding introducing bubbles. The MLS then places a transparent plastic qPCR film on the PMMP and seals the film with a plate sealer and spin briefly to remove bubbles with a plate spinner.

PCR Thermal Profile (Amplification Area) (Combined Saliva/Mucosa Testing):

Load the plate into a Bio-Rad CFX or a QuantStudio PCR machine, Open master file "ST-COV-PCR protocol", and run the following thermocycler conditions:

1. Step 1: 55° C. 10 minutes, 1 cycle;

2. Step 2: 95° C. 1 minute, 1 cycle; and

Step 3: 95° C. 10 sec, 60° C. 30 sec (+plate read at both FAM channel for N1 target & Cy5 channel for RNP target) for 40 cycles.

Data Interpretation (BioRad CFX Opus 96-Well Format) (Saliva/Mucosa Testing):

The Bio-Rad CFX reports Cq values, in which the Cq value files (csv file) are exported from the PCR machine to the OvDx LIMS. Interpretation of the Cq values (DETECTED, NOT DETECTED, and INVALID) will be exported to the OvDx LIMS according to the following criteria:

| | Cq: N1 (FAM channel) | Cq: RNP (Cy5 channel) |
|---|---|---|
| (COVID-19 positive) DETECTED | ≤36 | Any number or NaN |
| (COVID-19 negative) NOT DETECTED | >36 | ≤35 |
| INVALID | >36 | >35 |

If N1 is detected, the result is valid ad returns a "DETECTED" regardless of value for RNP. If N1 is NOT detected and RNP is <35, then return a result of "NOT DETECTED". If RNP Cq value >35 and if N1>36, then the sample is requeue for retesting. After retesting, if the RNP is still >35, then the provider must be contacted to collect another sample. NaN=not a number.

Quality Assurance and Batch Release (Saliva/Mucosa Testing):

The Lab Supervisor will examine the controls, including: positive control (2019-nCoV_N_Control, IDT), which should be positive for N1, but negative for RNP targets; Negative control (Hs_RPP30 Control), should be negative for N1, but positive for RNP targets; and NTC control should be negative for both N1 and RNP targets. The Lab Supervisor will further spot check run and estimate positive-negative results ratio. The Medical Director will release the batch and sign off on the report after further examination.

Samples Placement after PCR Testing (Saliva/Mucosa Testing):

Samples with INVALID results will be identified in the temporary sample storage area (fume hood 1). Repeated testing will be performed on these samples starting from Step III (Combined Saliva Respiratory Mucosa Sample Preparation). Samples with verified results will be stored at −80° C. PCR plates will be moved to the disposal area (fume hood 2) as biohazards.

On-Site Nasal Swab and Oropharyngeal Swab Sample Collection:

Nasal swab collection devices include: a 1.9 ml Nest tube filled with 1 ml a unique buffer composition specific to swab samples (hereinafter referred to as Swab Transport Buffer), which will be used as the container of the nasal swab sample; and an oral/Nares swab by Nest will be used to swab the patient's anterior nares and later be placed inside the Nest tube filled with the Swab Transport Buffer.

Oropharyngeal swab collection devices include an oral/ Nares swab by Nest that is used swab the patient's oropharynx. The swab with the oropharyngeal sample is placed into the Nest tube with the nasal swab and Swab Transport Buffer.

The nasal swab (anterior nares) and oropharynx swab should be collected under the supervision of a trained healthcare worker designated by the organization overseeing the collection site. The healthcare worker supervising the collection should clean hands with alcohol-based sanitizer or fragrance-free soap and water and don appropriate PPE (gown, gloves, face mask, and/or face shield). Before collection, patients are provided instructional materials. The healthcare worker ensures all patient information, including name, date of birth, and additional information required by state reporting rules, is filled out properly before collection. The healthcare worker then asks the patient to review a study consent form to opt in or out of the study (provided by Ovation). Lastly, the healthcare worker will scan a preprinted barcode label to tie it to the patient information that is already collected, then place the label on the Nest tube that will be used by the patient.

The healthcare worker removes the cap of the Nest tube, directs the patient to swab their anterior nares ten times for each nares, and breaks the swab inside the tube at the proximal breakpoint. The healthcare worker similarly obtains an oropharyngeal swab. The healthcare worker will replace the cap of the Nest tube with both swabs and make sure it's securely tightened. If there is any sample spill during the collection process, the healthcare worker will use an alcohol wipe or equivalent to wipe the outside of the tube to prevent contamination. The sample will then be placed in an individual bag under room temperature before being transported to the lab.

The healthcare worker supervising the swab sample collection should use alcohol-based hand sanitizer after handling each patient's sample.

Combined Swab Sample Receiving and Accessioning in Lab:

Combined swab samples are transported to the lab. Samples will be removed from bags and visually examined by the accessioning supervisor at the receipt desk for any leakage or damage. Samples passed the pre-screening step by the supervisor are moved to the desktop used by the accessioning team. Samples failed the pre-screening step are set aside for further investigation. Accessioners will scan the barcodes on the Nest tubes and examine patient information and consent status shown on a computer screen via a laboratory information management system (LIMS). Tubes with complete patient information in the LIMS and have no leakage (i.e., qualified samples), are placed in a rack. The positions of the samples in the rack should match assigned positions in the LIMS. Disqualified samples are placed in another rack and set aside for further investigation by the accessioning supervisor. The rack of samples may then be placed on a platform rocker in hold position @ 600 rpm until a medical lab scientist (MLS) from the sample preparation team fetches the samples.

Combined Swab Preparation Buffer:

As part of sample preparation, the swab sample will be mixed with a unique buffer composition prepared specifically for swab samples (referred to herein as Swab Preparation Buffer). Preparation of the Swab Preparation Buffer includes use of at least the following equipment: Biosafety cabinet or laminar flow hood (workspace capable of maintaining an aseptic environment); individual, sterile wrapped pipettes, pipette tips, such as 10 and 25 mL; pipette aid; pipettor, 1 mL or 200 μL and corresponding tips; 50 ml sterile, nuclease-free Falcon tubes; Eppendorf repeater (50 mL capacity); 1.9 ml Cryovial tubes, Nest; Nest tube racks; and screw cap tube decapper equipment, Brooks Life Sciences.

The preparation of the Swab Transport Buffer further includes use of at least the following reagents/components:

10×TBE Buffer (Tris-Borate-EDTA, pH 8.2-8.4), Sterile, DNase-, RNase- and Protease-Free grade, Fisher BioReagents, catalog number BP133320, 20 L;

RNase inhibitor, human placenta, 40,000 units/ml, Sterile, DNase-, RNase-Free grade, New England Biolabs, catalog number M0307L, 10,000 units, 250 ul/tube;

Amphotericin B solution, 250 μg/ml in deionized water, sterile, Sigma-Aldrich, catalog number A2942, 100 ml (or similar antifungal at an appropriate concentration to prevent fungal contamination and growth);

Penicillin-Streptomycin Solution, 100×, a mix of Penicillin (10,000 IU) and Streptomycin (10,000 μg/ml) in a 100-fold working concentration, Sterile, Corning, catalog number 30-002-CI (or similar antibiotics at an appropriate concentration to prevent bacteria contamination and growth;

Nuclease-free water, Sterile, Millipore/Sigma, W4502, DNase-, RNase- and Protease-Free grade; and Disinfectant, such as 70% ethanol.

Preparation of the ingredients includes at least the following steps: clean work surface with appropriate disinfectant; disinfect reagent bottles prior to placing on work surface; aliquot 10×TBE Buffer, 500 ml/bottle in Corning 500 ml sterile bottle, store at RT; aliquot nuclease-free water, 894.95 ml/bottle in Corning 1 L sterile bottle, store at RT; aliquot Amphotericin B solution 4 ml/tube (in 5 ml sterile Corning tube), store at −20 C; aliquot Penicillin/Streptomycin, 1 ml/tube (in sterile Eppendorf tubes), store at −20 C; and Record lot information and preparation in a laboratory-controlled notebook.

Preparation of the Swab Preparation Buffer includes at least the following steps:

1. Clean work surface with appropriate disinfectant;

2. Disinfect reagent bottles (aliquot, except RNase inhibitor) prior to placing on work surface;

3. For example, to prepare 1 L viral transport buffer:

3.1. bring 1 bottle of nuclease-free water (894.95 ml/bottle);

3.2. using a sterile 50 ml falcon tube, add 100 ml of 10×TBE Buffer;

3.3. using a sterile pipette, add 50 μl of RNase inhibitor; and 3.4 thaw a tube of Amphotericin B solution and a tube of Penicillin/Streptomycin, using a sterile pipette, aseptically add 4 ml of Amphotericin and 1 ml of Penicillin/ Streptomycin to the bottle.

4. Record lot information and preparation in a laboratory-controlled notebook;

5. Assign laboratory appropriate identification (e.g. lot number);

6. Cap the tube securely and mix thoroughly by inverting the tube;

7. Withdraw 100 ul of medium for QC sample;

8. Label the bottle as:

SWAB TRANSPORT BUFFER

Lab ID: (Insert laboratory appropriate identification, such as STB2 as Summit Buffer 2)

DOM: (Insert current date of manufacture)

Expires: (Insert date 1 month after manufacture date)

Store at 2-8 C

9. Store at 2-8 C, until dispensed into aliquots;

10. Aliquot 1 mL of prepared Swab Preparation Buffer into individual sterile 1.9 ml screw-capped tubes (Nest) using Eppendorf repeater (50 mL capacity) and Brooks decapper;

11. Perform sterility check; and

12. Store tubes and any buffer remaining in the bottle at 2-8 C.

Combined Swab Sample Preparation:

An MLS from the sample preparation team will fetch the racks of accessioned samples on the rocker and bring them into the sample preparation room to prepare them for testing. They will bring prepared 96-well Sample Prep Plate (SPP) containing 5 μL/well of protease (Proteinase K). In particular, the 96-well SPP contains 5 μL of Proteinase K (Promega))/well, dispensed into each well using a multichannel equalizer or Viaflow (Integra). Samples are decapped with a semi-automated 6-channel decapper (Brooks) or automated 48-format decapper (Brooks) inside the biosafety cabinets. Caps will be temporarily placed on the cap carrier rack when using the 6-channel decapper. Approximately 35 μL of swab sample are transferred from the tubes in the 48-well rack using the E1-ClipTip electronic multichannel (8-channels) equalizer to the 96-well SPP containing the 5 μL of Proteinase K and pipetting well. Two 48-well racks of samples will fill one 96-well SPP. Samples are recapped (6 at a time if using the 6-channel decapper or 48 at a time if using the automated 48-format decapper). The swab samples and Proteinase K are mixed well by placing the plates on the digital microplate shaker @ 500 RPM for 1 minute. The plate is placed on the miniAmp 96-well PCR instrument at 95° C. for 5 minutes, and 4° C. on hold. The entire racks of samples are then brought to the temporary sample storage area. Any of the samples that require repeat testing will be identified from the temporary sample storage area. Repeat testing is only allowed one time. If failed, request a new sample. Store left-over samples in −80° C. for future use.

PCR Reagent Preparation and Plate Setup (Combined Swab Testing):

A plate containing a PCR master mix (herein referred to as a PCR Master Mix Plate (PMMP), includes 12.5 μL of PCR master mix dispensed into each well of the plate using a multichannel equalizer or Viaflow (Integra) on to a 96- or 384-well plate. The PCR master mix is composed of 10 μL Luna Universal Probe One-Step Reaction Mix, 1 μL Luna Warmstart RT enzyme Mix, and 1.5 μL of N1/RNP primer/probe. The 1.5 μL N1/RNP primer/probe will be made as: 6.7 μM working stocks of the N1 and RNP primers and 1.7 μM FAM-labeled N1 and ATTO-647 labeled RNP probe by adding 50.25 μL of each 100 μM primers and probe stock to 524 μL IDTE buffer (pH7.5).

The MLS in the molecular team will place a 96- or a 384-well PMMP into their individual PCR workstation and add 7.5 μL of treated combined swab sample from the Swab Sample Preparation Step to each designated well of the PMMP. The treated combined swab sample is then mixed with the PCR master mix by pipetting, taking care to avoid introducing bubbles. The MLS then adds 7.5 μL of positive control (IDT synthetic 2019-SARS-CoV-N control, 4000 copies/uL), and negative control (IDT Hs-RPP30 control, 4000 copies/μL) for SARS-CoV-2, and no-template control (NTC—water) to designated PCR wells for the controls (1 positive control, 1 negative control, and NTC per plate) and mixes by pipetting, avoiding introducing bubbles. The MLS then places a transparent plastic qPCR film on the PMMP and seals the film with a plate sealer and spin briefly to remove bubbles with a plate spinner.

PCR Thermal Profile (Amplification Area) (Combined Swab Testing):

Load the plate into a Bio-Rad CFX or a QuantStudio PCR machine, Open master file "ST-COV-PCR protocol", and run the following thermocycler conditions:

1. Step 1: 55° C. 10 minutes, 1 cycle;

2. Step 2: 95° C. 1 minute, 1 cycle; and

Step 3: 95° C. 10 sec, 60° C. 30 sec (+plate read at both FAM channel for N1 target & Cy5 channel for RNP target) for 40 cycles.

Data Interpretation (BioRad CFX Opus 96-Well Format) (Combined Swab Testing):

The Bio-Rad CFX reports Cq values, in which the Cq value files (csv file) are exported from the PCR machine to the OvDx LIMS. Interpretation of the Cq values (DETECTED, NOT DETECTED, and INVALID) will be exported to the OvDx LIMS according to the following criteria:

| | Cq: N1 (FAM channel) | Cq: RNP (Cy5 channel) |
|---|---|---|
| (COVID-19 positive) DETECTED | ≤36 | Any number or NaN |
| (COVID-19 negative) NOT DETECTED | >36 | ≤35 |
| INVALID | >36 | >35 |

If N1 is detected, the result is valid ad returns a "DETECTED" regardless of value for RNP. If N1 is NOT detected and RNP is <35, then return a result of "NOT DETECTED". If RNP Cq value >35 and if N1>36, then the sample is requeue for retesting. After retesting, if the RNP is still >35, then the provider must be contacted to collect another sample. NaN=not a number.

Quality Assurance and Batch Release (Combined Swab Testing):

The Lab Supervisor will examine the controls, including: positive control (2019-nCoV_N_Control, IDT), which should be positive for N1, but negative for RNP targets; Negative control (Hs_RPP30 Control), should be negative for N1, but positive for RNP targets; and NTC control should be negative for both N1 and RNP targets. The Lab Supervisor will further spot check run and estimate positive-negative results ratio. The Medical Director will release the batch and sign off on the report after further examination.

Samples Placement after PCR Testing (Swab Testing):

Samples with INVALID results will be identified in the temporary sample storage area (fume hood 1). Repeated testing will be performed on these samples starting from Step III (Saliva Sample Preparation). Samples with verified results will be stored at −80° C. PCR plates will be moved to the disposal area (fume hood 2) as biohazards.

Example 3

In this example, the relative efficacies of anterior nasal swab (ANS) samples and saliva samples were compared for the detection of the SARS-CoV-2 virus. Briefly, an ANS sample was collected with DNA Genotek's OR-100 device (SwabClear™), and a saliva sample was collected using DNA Genotek's OM-505 device (SalivaClear™) from the same patients. Samples were run to detect SARS-CoV-2 virus in accordance with the manufacture's instructions.

Although most paired samples showed consistent results (detection in both or non-detection in both) between ANS and saliva samples, discordant results between the two types of specimen were observed in some paired samples (i.e., detection of SARS-CoV2 in one specimen but non-detection in the other). Based these clinical observations, it was hypothesized that the abundance or clearance of SARS-CoV-2 or other respiratory viruses can vary in nasal cavity vs. in saliva across individuals or at different points of time during the course of the infection or disease. Thus, tests relying on only one specimen site can mean missing some SARS-CoV-2 positive cases.

Consequently, a test combining the nasal cavity swab and saliva specimens maximize the chance of detection of SARS-CoV-2 or other respiratory viruses among diverse populations and at different points of time during the infection or disease course.

Example 4

This example provides experimental results showing the improvement in enriched viral abundance detected in combined saliva and anterior nares nasal swab samples compared with paired saliva-only samples.

Sixteen human participants spit saliva samples into 50 ml falcon tubes. A flocked nasopharyngeal swab was used to collect anterior nares swab (ANS) samples from the same participants. One saliva sample from each patient was used in the RNA-extraction free qPCR protocol in accordance with Examples 1-2 to detect a SARS-CoV-2 infection. The nasal swabs were placed swab down in falcon tube holding a second saliva sample from each participant. The swabs were squeezed to extract the ANS sample and mix it with the saliva. The combined saliva and ANS samples underwent the same RNA-extraction free qPCR protocol as the saliva samples.

Figure 3:
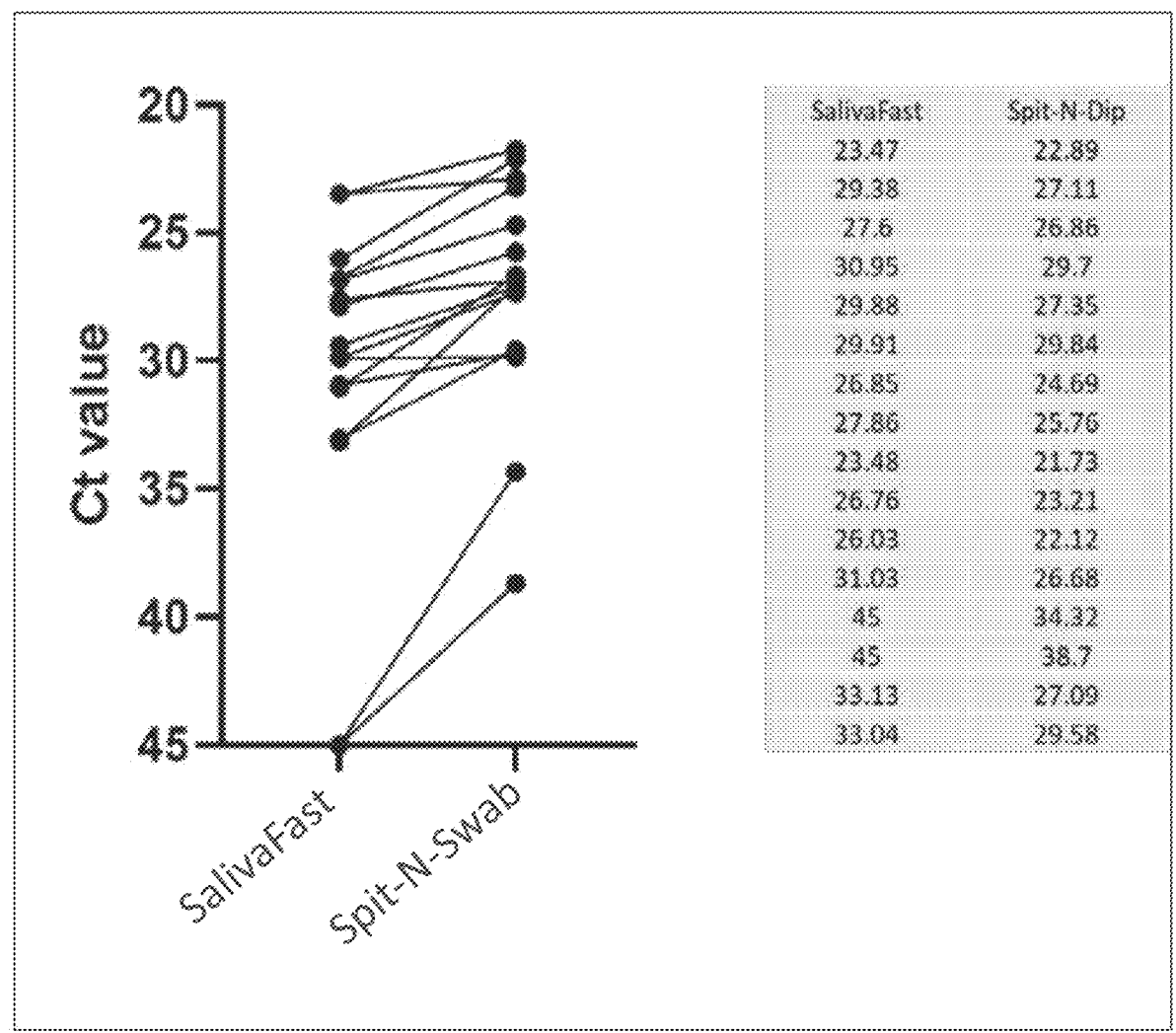
FIG. 3 shows results for a SARS-CoV-2 qPCR detection protocol performed on paired saliva-only and combined saliva and nasal swab samples obtained from the same patients.

FIG. 3 provides the qPCR results as cycle threshold (Ct) values, which indicate how much SARS-CoV-2 virus was detected in the sample. The paired results for the saliva-only samples are provided as "SalivaFast" and the combined samples as "Spit-N-Dip".

This data shows a significant improvement of enriched viral abundance (shown as lower Ct value) in the mixed ANS-Saliva specimens when compared to testing using only saliva using the same testing protocol.

Thus, combined samples clearly provide more sensitive results when compared to samples obtained from a single source.

It is thus anticipated that combining other types of nasal swabs, such as nasopharyngeal and mid-turbinate, and mixing such specimen with saliva would generate similar improved results among individuals who might have different viral load levels for detection purposes in different specimen locations. Similarly, it is also possible to combine nasal swabs with oropharyngeal swabs as a mixed specimen. Therefore, although the test provided in this example focuses on combining ANS and saliva as a specimen for testing of SARS-CoV-2 and other respiratory viruses, this general method of mixing specimens from different locations in the human body maximizes the chance for viral detection while lowering initial testing cost. This method can also be viewed as a "pooling" technique of combining specimens from different body locations in the same person.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A method for extraction-free analysis of nucleic acid, the method comprising the steps of:
   mixing a combined saliva sample and respiratory mucosa sample in a buffer composition comprising nuclease-free water, an antifungal, an antibiotic, a reducing agent, and a ribonuclease inhibitor;
   directly amplifying nucleic acid from the sample in said buffer with primers specific to a target nucleic acid without prior extraction of said nucleic acid; and
   analyzing amplicons produced in said amplifying step to detect presence of a pathogen.

2. The method of claim 1, wherein said nucleic acid is a pathogen.

3. The method of claim 2, wherein said pathogen is a virus or a bacterium.

4. The method of claim 3, wherein the virus comprises a coronavirus or an influenza virus.

5. The method of claim 4, wherein the coronavirus is severe acute respiratory syndrome coronavirus-2 (SARS-COV-2).

6. The method of claim 5, wherein the method further comprises analyzing the amplicons to detect the presence of one or more target SARS-COV-2 variants.

7. The method of claim 6, wherein the method does not include amplification of a wildtype SARS-COV-2 nucleic acid.

8. The method of claim 4, wherein the nucleic acid specific primers target one or more of the virus's N, ORF lab, and E genes.

9. The method of claim 1, wherein prior to mixing the method comprises obtaining the saliva sample in a vessel and placing a nasal swab comprising the respiratory mucosa sample into the saliva sample in the vessel.

10. The method of claim 9, further comprising squeezing and/or agitating the nasal swab in the sample vessel to mix the saliva sample and respiratory mucosa sample.

11. The method of claim 9, wherein the nasal swab comprises a respiratory mucosa sample from one or more locations in a nasal cavity.

12. The method of claim 11, wherein the one or more locations comprise an anterior nares, a mid-turbinate, and/or a nasopharynx.

13. The method of claim 12, wherein the respiratory mucosa sample is obtained from the anterior nares.

14. The method of claim 1, wherein said nucleic acid is RNA or DNA.

15. The method of claim 1, further comprising the step of comparing nucleic acid quantities in a plurality of combined saliva sample and respiratory mucosa samples obtained from a patient at successive time points and determining disease progression based on increases or decreases in the nucleic acid quantities over time.

16. The method of claim 15, further comprising the step of predicting disease outcomes based on the nucleic acid quantity.

17. A method for extraction-free analysis of nucleic acid, the method comprising the steps of:

providing a vial;

obtaining a saliva sample from a subject in the vial;

obtaining a respiratory mucosa swab sample from the subject;

mixing the saliva sample and respiratory mucosa swab sample in the vial with a buffer composition comprising nuclease-free water, an antifungal, an antibiotic, a reducing agent, and a ribonuclease inhibitor;

directly amplifying nucleic acid from the sample in said buffer with primers specific to a target nucleic acid without prior extraction of said nucleic acid; and analyzing amplicons produced in said amplifying step to detect presence of a pathogen.

18. A kit for performing the method of claim 17, the kit comprising:

the vial;

a saliva collection aid or a funnel;

the buffer composition;

the primers specific for the target nucleic acid; and instructions for extraction-free analysis of nucleic acid.

19. A method for stabilizing a viral sample, the method comprising the steps of obtaining a body fluid sample suspected of containing a virus;

adding to the body fluid sample a buffer comprising nuclease-free water, an antifungal, an antibiotic, a reducing agent, and a ribonuclease inhibitor thereby to stabilize the virus; and transporting the sample to a testing site.

* * * * *